(12) United States Patent
Petty

(10) Patent No.: US 10,768,116 B2
(45) Date of Patent: *Sep. 8, 2020

(54) MULTI-FLUID TEST STRIP

(71) Applicant: Jon A. Petty, St. George, UT (US)

(72) Inventor: Jon A. Petty, St. George, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/390,371

(22) Filed: Apr. 22, 2019

(65) Prior Publication Data

US 2019/0242828 A1    Aug. 8, 2019

Related U.S. Application Data

(63) Continuation of application No. 14/929,953, filed on Nov. 2, 2015, now Pat. No. 10,281,407.

(51) Int. Cl.

| | | |
|---|---|---|
| *G01N 21/78* | (2006.01) | |
| *G01N 21/84* | (2006.01) | |
| *G01N 21/80* | (2006.01) | |
| *G01N 33/20* | (2019.01) | |
| *G01N 21/75* | (2006.01) | |
| *G01N 21/77* | (2006.01) | |

(52) U.S. Cl.
CPC .............. *G01N 21/78* (2013.01); *G01N 21/80* (2013.01); *G01N 21/8483* (2013.01); *G01N 33/20* (2013.01); *G01N 2021/752* (2013.01); *G01N 2021/7759* (2013.01); *G01N 2021/7793* (2013.01)

(58) Field of Classification Search
CPC ...... G01N 21/78; G01N 31/22; G01N 21/293; G01N 2021/7759; G01N 21/80; G01N 21/8483; G01N 33/2835; G01N 21/29; G01N 2021/752; G01N 2021/7793
See application file for complete search history.

(56) References Cited

U.S. PATENT DOCUMENTS 10,281,407 B2 *  5/2019  Petty ................... G01N 21/8483

OTHER PUBLICATIONS

"All-in-1 Multi-Fluid Test Kit", ACUSTRIP Company, Inc, Mountain Lakes, NJ (showing interstate sale on Aug. 10, 2011) (3 pgs.)

* cited by examiner

*Primary Examiner* — Dennis White
*Assistant Examiner* — Bryan Kilpatrick
(74) *Attorney, Agent, or Firm* — David Meibos; Maywood IP Law

(57) ABSTRACT

A multi-fluid test strip may include a first zone to test a first fluid, a second zone to test a second fluid, and a third zone intermediate the first zone and the second zone. The third zone may prevent cross-contamination of the first fluid with the second zone and prevent cross-contamination of the second fluid with the first zone. The multi-fluid test strip may also include a first grip zone and a second grip zone. The first zone may be intermediate the first grip zone and the third zone and the second zone may be intermediate the second grip zone and the third zone. The first grip and second grip zones may be dimensioned to permit gripping of the first and second grip zones without touching the first or second zones.

20 Claims, 6 Drawing Sheets

MULTI-FLUID TEST STRIP

CROSS-REFERENCE TO RELATED APPLICATIONS

This application is a continuation of U.S. application Ser. No. 14/929,953 filed Nov. 2, 2015, U.S. Pat. No. 10,281,407, entitled "Multi-Fluid Test Strip", which is incorporated herein by reference in its entirety.

The present application is related to:

U.S. Pat. No. 6,651,487, entitled TEST FOR BRAKE FLUID AGE AND CONDITION, which issued on Nov. 25, 2003;

U.S. Pat. No. 6,691,562, entitled TEST FOR BRAKE FLUID AGE AND CONDITION, which issued on Feb. 17, 2004;

U.S. Pat. No. 6,796,339, entitled APPARATUS FOR FLUSHING, REPLACING FLUID AND BLEEDING HYDRAULIC SYSTEMS, which issued on Sep. 28, 2004;

U.S. Pat. No. 7,152,636, entitled BRAKE FLUSH ACCELERATOR, which issued on Dec. 26, 2006;

U.S. Pat. No. 7,682,834, entitled COLORIMETRIC TEST FOR BRAKE FLUID, which issued on Mar. 23, 2010;

U.S. Pat. No. 8,021,890, entitled COLORIMETRIC TEST FOR BRAKE SYSTEM CORROSION, which issued on Sep. 20, 2011;

U.S. Pat. No. 8,216,849, entitled COLORIMETRIC TEST FOR BRAKE SYSTEM CORROSION, which issued on Jul. 10, 2012; and U.S. Pat. No. 8,464,763, entitled BRAKE FLUSH MACHINE, which issued on Jun. 18, 2013.

The foregoing documents are incorporated by reference as though set forth herein in their entirety.

TECHNICAL FIELD

The present disclosure relates to testing fluids. More specifically, the present disclosure relates to a multi-fluid test strip that may test various aspects of multiple fluids, such as brake fluid and coolant fluid.

BACKGROUND

Brake fluid is used to transmit the pressure exerted on a motor vehicle's brake pedal to the slave cylinders of the braking system. The most commonly used brake fluids in North America consist of glycol-based liquids categorized as DOT3 and DOT4 based on the boiling point resulting from their particular composition. In order to prevent boiling of the fluid caused by overheating during use, DOT3 and DOT4 fluids are required to have a dry boiling point (with no moisture in fluid) of at least 401° F. (205° C.) and 446° F. (230° C.), respectively, so that proper brake operation is ensured under all temperature conditions.

All types of glycol-based brake fluid are hygroscopic. As a result of this property, they readily absorb moisture that reduces their boiling point.

Another important aspect of brake systems maintenance is the corrosive nature of some of their constituents, which, upon contamination of the brake fluid, progressively contribute to damage of metallic tubing and other parts of the brake system. Most brake lines consist of steel lined with a copper alloy. Brake lines typically represent the largest surface area of metal in contact with brake fluid. A typical light-duty vehicle uses about 14 meters of such copper-lined steel tubing with an inside diameter of about 2.5 mm, for a total internal surface area of about 1,200 cm². Therefore, corrosion of these lines contributes relatively large amounts of copper ions to the fluid. The master and slave cylinders and antilock brake system (ABS) include components made of steel, aluminum, zinc, or other materials that are also susceptible to corrosion as the fluid ages, its water content increases and its reserve alkalinity decreases. Dissolved iron is also known to appear in brake fluid after the initial amine corrosion inhibitor is significantly depleted and the dissolved copper level reaches about 200 ppm. By the time this event occurs, the brake fluid is highly corrosive and damaging to the brake system and its replacement is called for regardless of its actual service time or mileage.

Corrosion inhibitors in new brake fluid inhibit corrosion initially. In conventional brake fluids, amines are included in the new brake fluid to inhibit corrosion and prevent damage to metal parts that operate in contact with the fluid. Corrosion inhibitors deplete with time, temperature, and environmental stress (for example, air, moisture, salts, ions, and other contaminants seeping into the fluid). As the corrosion inhibitors deplete, corrosion accelerates. As the brake fluid ages, its anticorrosive properties are measured in terms of reserve alkalinity; that is, the amount of amines remaining in the fluid to buffer the pH, or acidity, resulting from breakdown of fluid constituents. Over time, thermal oxidation and volatization produce a significant reduction of the amine content and the concurrent decrease of anticorrosive properties. Tests have shown that the reserve alkalinity of DOT3 and DOT4 fluids is reduced to about 20 percent of its original value after 18 to 20 months of normal operation.

Corrosion in the brake system is harmful, and at some point, internal corrosion may interfere with the proper operation of the brakes or antilock brake system (ABS). Copper deposition onto brake system components, particularly ABS seats and valves, is also undesirable and may interfere with the proper operation of the brakes or ABS. A finite level of copper ions in brake fluid with water will cause corrosion of ferrous metals like iron, cast iron, steel, and the like in the brake system. The level of copper ions in brake fluid with water (as low as 2% water) is an indicator of the virtual age of the brake fluid and the potential for corrosion of ferrous metals.

Copper is of interest in brake system corrosion because copper can form stable ions in water-free (dry) inhibited commercial brake fluid, and thus copper can begin corroding immediately upon contact with brake fluid in the presence of oxygen. Copper is also an oxidizer for other metals. Iron ions, on the other hand, have limited solubility in dry commercial brake fluid. Iron begins to corrode when brake fluid takes on water and/or the corrosion inhibitors become depleted. Iron may be oxidized by oxygen, water, and copper ions in the brake fluid. Copper oxidizes iron in the same manner as oxygen, with a copper ion gaining an electron from an iron atom, plating or depositing a copper atom on or near the iron substrate, and releasing an iron ion into solution. The copper level in brake fluid is directly proportional to the corrosivity of the brake fluid, or its potential corrosivity.

However, copper is not the only species of interest in brake system corrosion. Iron, zinc, tin, aluminum, and brass (an alloy of copper and zinc) are also found in brake systems, and these materials are susceptible to corrosion. Any of these materials, or their ions, may be referred to as a reactive constituent of brake fluid because of their susceptibility to corrosion.

Therefore, brake fluids also need to be checked and periodically replaced in order to prevent dangerous corrosion in the brake system. Accordingly, industry maintenance recommendations, where such exist, are typically based on service time and mileage of the vehicle.

U.S. Pat. No. 6,691,562 discloses an approach for estimating service time and/or mileage of brake fluid based on the recognition that the copper content in brake fluid is predictably related to time and mileage of vehicle operation. Thus, this correlation can be advantageously used to estimate milestones for maintenance purposes without regard to actual service time and/or mileage. Instead, copper content is adopted as a reliable indicator of a brake system's or a vehicle's "virtual age," a term used to refer to the wear and tear on brake fluid resulting from actual mileage, actual service conditions, and/or time of service.

In addition to brake fluid, most automobiles also use a coolant fluid to remove waste heat from the engine. Coolant fluids are typically a mixture of water and a glycol based antifreeze (such as ethylene glycol or propylene glycol) that also includes corrosion inhibitors to help protect the vehicles' radiator from a range of electrochemically incompatible metals such as aluminum, cast iron, copper, brass, solder, and the like.

When ethylene glycol is used in a radiator system, it may become oxidized to five organic acids: formic, oxalic, glycolic, glyoxalic, and acetic acid. Inhibited ethylene glycol antifreeze mixes are available, with additives that buffer the pH and reserve alkalinity of the solution to prevent oxidation of ethylene glycol and formation of these acids. Nitrites, silicates, theodin, borates and azoles may also be used to prevent corrosive attack on metal. However, over time, these pH buffers typically become depleted along with the reserve alkalinity of the coolant fluid as pH levels drop and acidity rises. When this occurs, the coolant fluid should be changed in order to avoid damage to the vehicles' radiator system.

Improper mixing or ratios of glycol-based antifreezes is another issue that commonly arises with mixed coolant fluids. For example, ratios of 50% glycol based antifreeze to 50% water on up to 70% glycol based antifreeze to 30% water are typically recommended. However, when coolant fluid levels need to be replenished, often times a user (not shown) will add only water or only glycol based antifreeze to the radiator system. Thus, over time the ratio of glycol based antifreeze to water may not be known.

Other vehicular fluids such as oil, transmission fluid, and the like also have chemical properties that should preferably be kept within specified ranges. Unfortunately, existing testing methods for coolant brake fluid, and/or other vehicular fluids are typically too cumbersome in the aggregate. In many instances, multiple separate testing devices must be used to provide a complete battery of tests for a vehicle. Hence, coolant, brake fluid, and/or other vehicular fluids may only be infrequently tested. Performing a complete battery of tests may be time and/or cost prohibitive. Accordingly, many individuals continue to operate their vehicles under unsafe conditions, unaware that one or more vehicular fluids require replacement or remediation.

SUMMARY

In some embodiments, a multi-fluid test strip may include a first zone to test a first fluid, a second zone to test a second fluid, and a third zone intermediate the first zone and the second zone. The third zone may prevent cross-contamination of the first fluid with the second zone and prevent cross-contamination of the second fluid with the first zone. The multi-fluid test strip may also include a first grip zone and a second grip zone. The first zone may be intermediate the first grip zone and the third zone and the second zone may be intermediate the second grip zone and the third zone. The first grip and second grip zones may be dimensioned to permit gripping of the first and second grip zones without touching the first or second zones.

In other embodiments, a method of testing multiple fluids may include utilizing a multi-fluid test strip that has a first zone to test a first fluid, a second zone to test a second fluid, and a third zone intermediate the first zone and the second zone. The third zone may prevent cross-contamination of the first fluid with the second zone and prevent cross-contamination of the second fluid with the first zone. The method may also include bringing the first zone into contact with the first fluid such that the third zone avoids contamination of the second zone with the first fluid and bringing the second zone into contact with the second fluid such that the third zone avoids contamination of the first zone with the second fluid. The method may further include observing one or more metrics associated with the first fluid created by the first zone reacting with the first fluid, and observing one or more metrics associated with the second fluid created by the second zone reacting with the second fluid.

In yet other embodiments, a multi-fluid test strip may include a first zone to test a first fluid with a first test pad, a second zone to test a second fluid with a second and third test pad, and a third zone intermediate the first zone and the second zone. The third zone may prevent cross-contamination of the first fluid with the second zone and prevent cross-contamination of the second fluid with the first zone. In at least one embodiment, the third zone may have a length greater than about 2.5 inches. The multi-fluid test strip may also include a first grip zone and a second grip zone. The first zone may be intermediate the first grip zone and the third zone and the second zone may be intermediate the second grip zone and the third zone. The first grip and second grip zones may be dimensioned to permit gripping of the first and second grip zones without touching the first or second zones.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Embodiments disclosed herein are generally discussed in the context of brake fluid and coolant fluid for simplicity. However, it will be understood that other fluids may also be used with the present disclosure including, but not limited to hydraulic fluids, internal combustion engine oils, non-internal combustion engine oils, transmission fluids, power steering fluids, hydraulic clutch fluids, shock/strut oils, differential fluids, and the like.

Figures 1A, 1B, 1C:
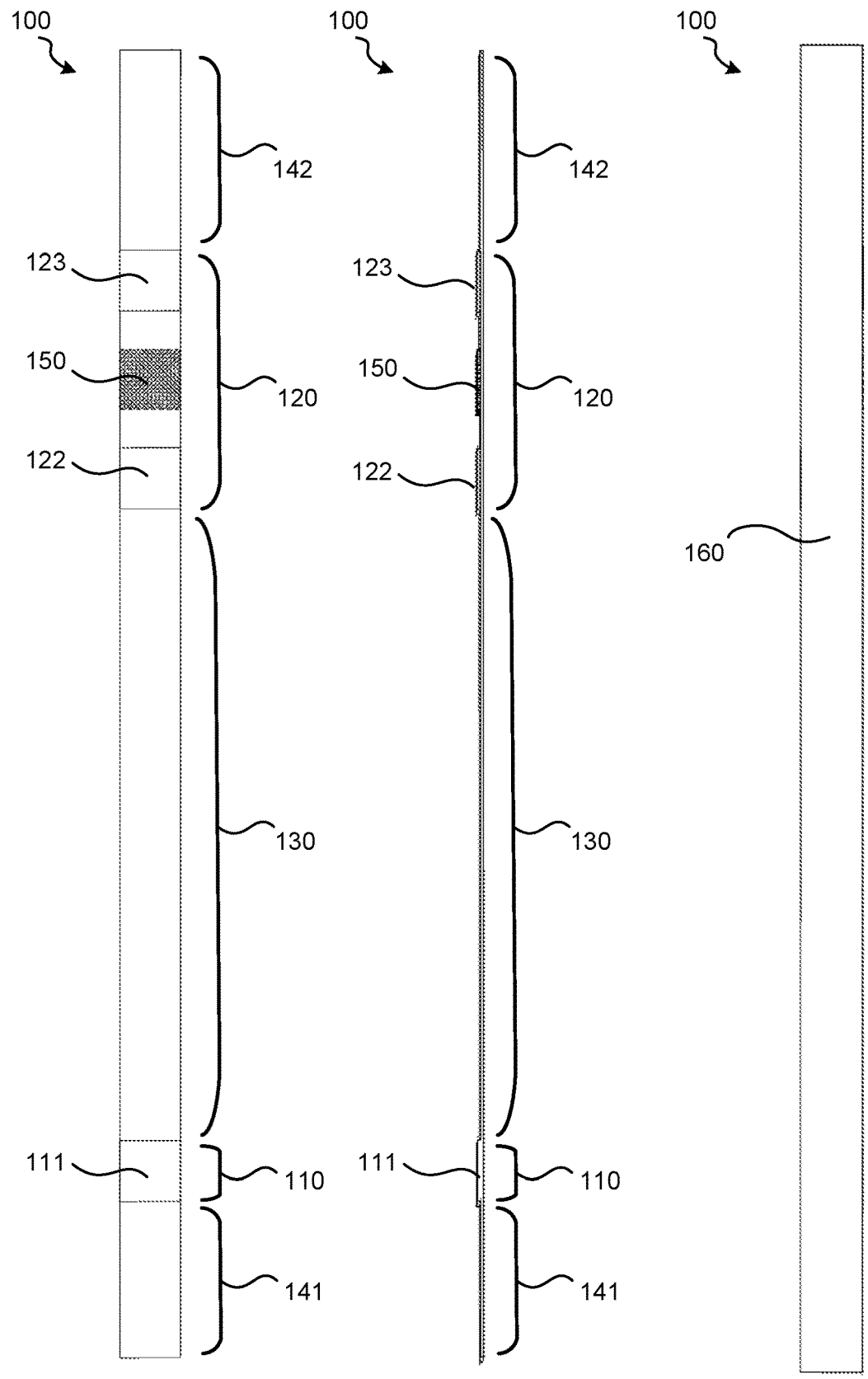
FIG. 1A is a front view of a multi-fluid test strip, according to one embodiment of the present disclosure.
FIG. 1B is a side view of the multi-fluid test strip of FIG. 1A.
FIG. 1C is a back view of the multi-fluid test strip of FIG. 1A.

FIGS. 1A-1B illustrates various view of a multi-fluid test strip 100, according to one embodiment of the present disclosure. The multi-fluid test strip 100 may include a first zone 110, a second zone 120, a third zone 130, a first grip zone 141, a second grip zone 142, and a substrate 160 that passes through the first zone 110, the second zone 120, the third zone 130, the first grip zone 141, and the second grip zone 142. The first zone 110 may be configured to test a first fluid (not shown) and the second zone 120 may be configured to test a second fluid (not shown). The third zone 130 may be intermediate the first zone 110 and the second zone 120 and configured to prevent cross-contamination of the first fluid with the second zone 120 and prevent cross-contamination of the second fluid with the first zone 110.

The first zone 110 may be intermediate the first grip zone 141 and the third zone 130. Likewise, the second zone 120 may be intermediate the second grip zone 142 and the third zone 130. The first grip zone 141 may be dimensioned to permit gripping of the first grip zone 141 without touching the first zone 110 and, similarly, the second grip zone 142 may be dimensioned to permit gripping of the second grip zone 142 without touching the second zone 120. For example, in some embodiments the first and/or second grip zones 141, 142 may have a length of about 0.3 inches to about 0.5 inches. In other embodiments, the first and/or second grip zones 141, 142 may have a length of about 0.5 inches to about 0.7 inches. In further embodiments the first and/or second grip zones 141, 142 may have a length of about 0.7 inches to about 1.0 inches. In still other embodiments the first and/or second grip zones 141, 142 may have a length less than about 0.3 inches. In yet further embodiments the first and/or second grip zones 141, 142 may have a length greater than about 1.0 inches.

In the embodiment shown in FIGS. 1A-1C, the first zone 110 may include a first test pad 111 configured to test a first aspect of the first fluid. The second zone 120 may also include a second test pad 122 configured to test a second aspect of the second fluid, as well as a third test pad 123 configured to test a third aspect of the second fluid. However, it will be understood that any number of test pads may be used in either the first zone 110 or the second zone 120.

The second test pad 122 and the third test pad 123 may be separated from each other by a barrier 150 and/or spaced apart from each other perpendicular to a length of the multi-fluid test strip 100. However, in other embodiments test pads may be spaced apart from each other perpendicular to a length of the multi-fluid test strip 100, or at any other angle relative to a length of the multi-fluid test strip 100. The barrier 150 may generally act to prevent or reduce flow of the second fluid between the second test pad 122 and the third test pad 123 to prevent color reaction contamination. For example, if color from the second test pad 122 is able to flow to the third test pad 123 (or vice versa), then the color of the reaction(s) may be inaccurate.

In at least one embodiment, the barrier 150 is a cross-hatch zone formed in the multi-fluid test strip 100 that is configured to reduce or prevent fluid flow between the second test pad 122 and the third test pad 123. In at least one embodiment, the cross-hatch zone may be a pattern formed in the multi-fluid test strip 100 by pressing the multi-fluid test strip 100 with a suitable tool (not shown) that has a cross-hatch pattern. The crosshatch zone may resist flow of the second fluid between the second test pad 122 and the third test pad 123 due to compressing of the multi-fluid test strip 100, which acts to reduce fluid flow across the cross-hatch zone by reducing capillary action forces inside the compressed material of the multi-fluid test strip 100. Additionally, the orientation and pattern of the intersecting lines in the cross-hatch zone may also act to reduce flow of the second fluid over the surface of the multi-fluid test strip 100 because the intersecting lines may form ridges that resist fluid flow and/or may direct fluid flow in one or more directions away from the test pads.

In at least one embodiment, the cross-hatch zone reduces or prevents fluid flow for an amount of time that is substantially long enough to allow the reactions of each test pad to take place without appreciable risk of cross-contamination between the test pads. In other embodiments, the crosshatch pattern may be formed by applying a glue or adhesive onto the multi-fluid test strip 100 in a crosshatch pattern. The orientation of the glue pattern in the cross-hatch zone may act to reduce flow of the second fluid over the surface of the multi-fluid test strip 100 because intersecting lines in the glue pattern may form ridges that may resist and/or direct fluid in one or more directions away from the test pads.

In other embodiments, the barrier 150 may include a mechanical barrier (not shown) that is configured to reduce or prevent flow between the second test pad 122 and the third test pad 123. In this embodiment, the mechanical barrier may include a nonpermeable material (or an at least semi-nonpermeable material) such that the second fluid is substantially prevented from flowing inside the nonpermeable material to cross-contaminate the test pads. Example nonpermeable materials may include, but are not limited to plastic materials, metals, rubber materials, silicone materials, and the like. The nonpermeable material may be placed between the second test pad 122 and the third test pad 123 as shown in FIGS. 1A-1C. The nonpermeable material may also include structures, such as ridges or patterns (not shown), that may further reduce fluid flow over the surface of the mechanical barrier.

In some embodiments (not shown), a mechanical barrier may encircle a substrate to define a coating that serves to block motion of the liquid along the substrate, between pads. Additionally or alternatively, in some embodiments, a barrier and/or the substrate may utilize hydrophobic materials, hydrophilic materials, and/or combinations thereof to avoid and/or control the flow of liquid along the test strip.

In other embodiments, the barrier 150 may include a length of test strip that is sufficiently long enough to effectively reduce or prevent fluid flow between test pads for an amount of time that is sufficiently long enough to allow the reactions of each test pad to take place without appreciable risk of cross-contamination between the test pads. In this embodiment, the length of test strip between the test pads may vary depending on the characteristics of each test pad. For example, the length of test strip between the test pads may depend on the tendency of a given test pad to leech chemicals or color dyes and/or the specific sensitivity of a given adjacent test pad to the leeched chemicals or color dyes.

The third zone 130 may also include a length of test strip that is sufficiently long to effectively reduce or prevent fluid flow between the first zone 110 and the second zone 120. The third zone may also include one or more barriers (not shown), such as crosshatch zones and/or one or more mechanical barriers, as discussed above. In at least one embodiment, the third zone 130 may have a length of test strip that is within the range of 0.25 inches to 1.5 inches. More specifically, the third zone 130 may have a length within the range of 0.5 inches to 1.0 inches. Yet more specifically, the third zone 130 may have a length within the range of 0.6 inches to 0.8 inches. Still more specifically, the third zone 130 may have a length of about 0.7 inches. In other embodiments, the third zone 130 may have a length of test strip that is between about 0.7 inches and about 2.5 inches. In yet further embodiments, the third zone 130 may have a length of test strip that is greater than about 2.5 inches. In such embodiments, the longer length of the third zone 130 may help facilitate the fluid testing process because longer test strips may better reach fluids that are housed deep within a container and/or reach fluids that may be hard to access because the container holding the fluid may have a small opening.

A gripping tool (not shown), such as a clip, an alligator clip, and the like, may also be used to grip the multi-fluid test strip 100 by one of its gripping zones to facilitate fluid testing in hard to reach places. The gripping tool may also reduce the likelihood of accidental contamination of the test pads by a user's fingers and prevent damage to the test pads by attaching the gripping tool to the grip zones of the multi-fluid test strip 100.

Figures 4A, 4B:
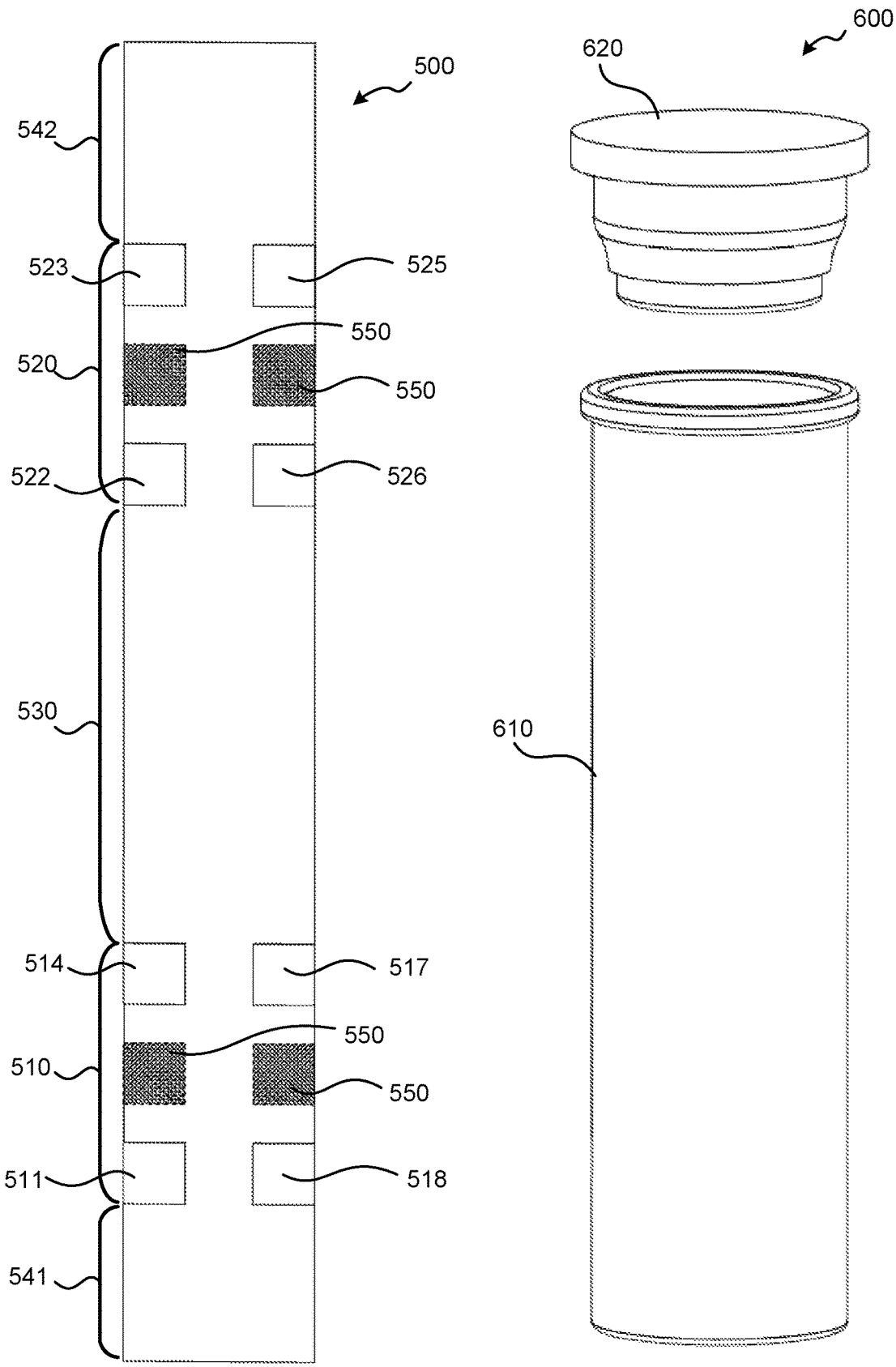
FIG. 4A is a front view of a multi-fluid test strip, according to another embodiment of the present disclosure.
FIG. 4B is an isometric view of a multi-fluid test strip container, according to one embodiment of the present disclosure.

Longer test strips may also be folded in half so they can more easily fit inside a suitable storage container, such as the multi-fluid test strip container 600 shown in FIG. 4B. The multi-fluid test strip container 600 shown in FIG. 4B may include a container lid 620 and a container body 610. The container lid 620 may be configured to have a tight seal with the container body 610 to protect the multi-fluid test strips 100 from atmospheric humidity and other environmental contaminants in order to increase the shelf life of the multi-fluid test strips 100. The container lid 620 may also include a desiccant or molecular sieve that further helps protect the multi-fluid test strips 100 from atmospheric humidity and other environmental contaminants.

In at least one embodiment, the first fluid may be a brake fluid and the second fluid may be a coolant fluid. In general, both of these fluids may be tested as part of a battery of tests performed synchronously or in close succession with the multi-fluid test strip 100 shown in FIGS. 1A-1C (or other test strips disclosed herein) by placing at least a portion of the brake fluid on the first zone 110, and placing at least a portion of the coolant fluid on the second zone 120.

The first test pad 111 may be configured to test a first metric associated with the brake fluid by reacting with the brake fluid to produce a first color change representative of the first metric associated with the brake fluid. The first metric may represent at least one of a copper level, an iron level, a DOT fluid type, and a first pH level of the brake fluid. Likewise, the second test pad 122 and the third test pad 123 may each be configured to test a second metric and a third metric associated with the coolant fluid by reacting with the coolant fluid to produce a second color change and a third color change representative of the second metric and the third metric associated with the coolant fluid. The second metric and the third metric may represent at least one of a glycol level, a reserve alkalinity, and a second pH level of the coolant fluid. In at least one embodiment, the second test pad 122 and the third test pad 123 may be configured to produce a substantially similar second color change and a substantially similar third color change for more than one type of coolant fluid. For example, the second test pad 122 and the third test pad 123 may produce a substantially similar second color change and a substantially similar third color change regardless of whether ethylene glycol based coolant fluids or propylene glycol based coolant fluids are used during the test. In at least one embodiment, the second test pad 122 may be configured to test a pH of the coolant fluid and the third test pad 123 may be configured to test a glycol level of the coolant fluid.

Each of the color changes disclosed herein may be compared against one or more color scales or color charts to ascertain an aspect or metric associated with the fluid under test. The one or more color scales or color charts may be further integrated together onto a single reference guide to simplify the test process. Color scales and charts are more fully discussed in the documents incorporated herein by reference, which are listed above.

Figure 2A:
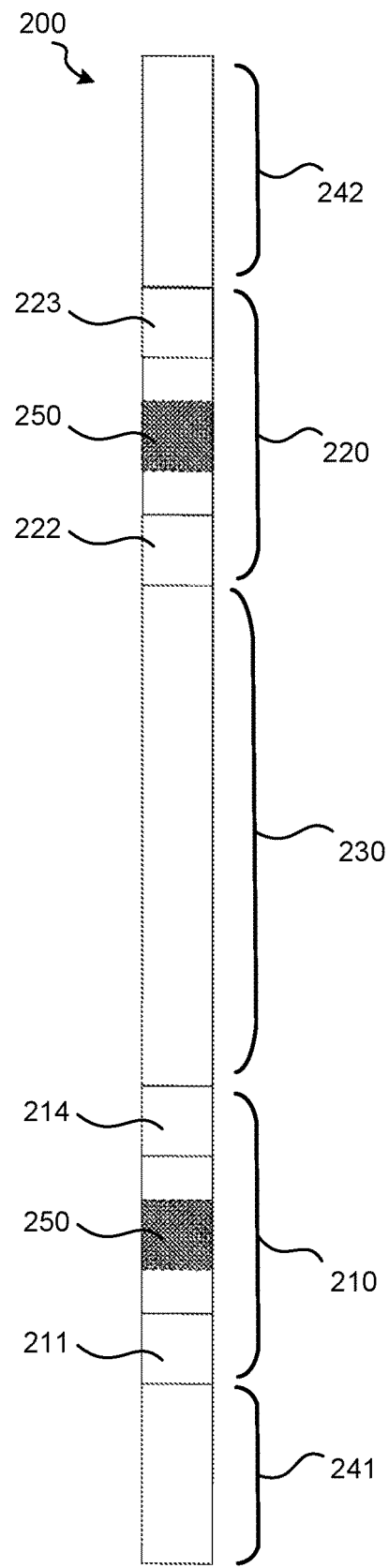
FIG. 2A is a front view of a multi-fluid test strip, according to another embodiment of the present disclosure.
Figure 2B:
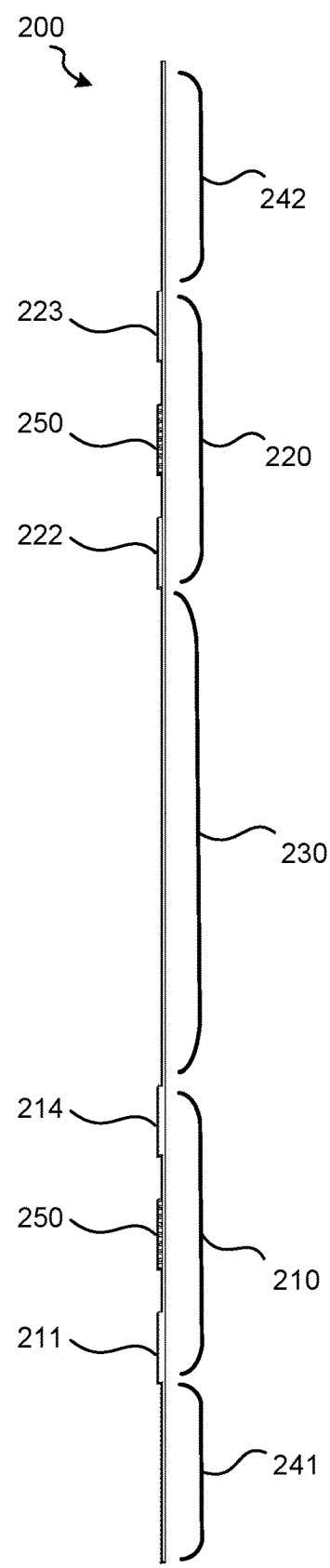
FIG. 2B is a side view of the multi-fluid test strip of FIG. 2A.
Figure 2C:
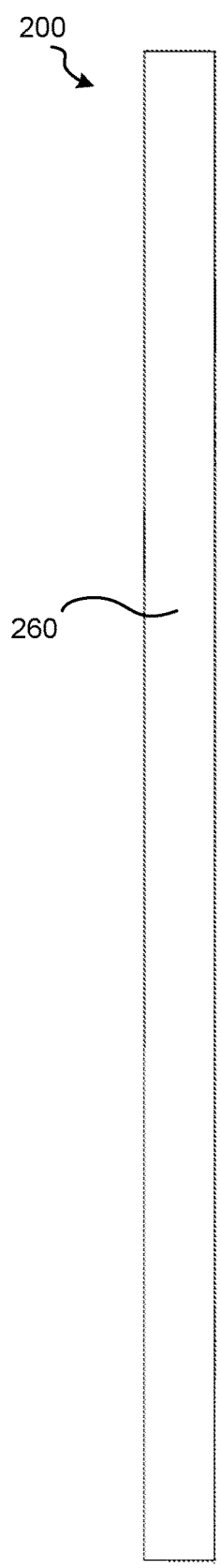
FIG. 2C is a back view of the multi-fluid test strip of FIG. 2A.

FIGS. 2A-2C illustrate various views of a multi-fluid test strip 200, according to another embodiment of the present disclosure. The multi-fluid test strip 200 may include similar features to the multi-fluid test strip 100 of FIGS. 1A-1C, such as: a first zone 210, a first test pad 211, a second zone 220, a second test pad 222, a third test pad 223, a third zone 230, a first grip zone 241, a second grip zone 242, one or more barriers 250, and a substrate 260. However, the multi-fluid test strip 200 may also include additional features, such as a fourth test pad 214 that may be separated from the first test pad 211 by one or more barriers 250. The fourth test pad 214 may be configured to measure an additional metric of a brake fluid, such as a copper level, an iron level, a DOT fluid type, and a first pH level of the brake fluid. It will be understood that any of the test strips disclosed herein may also include any number of test pads.

Figure 3A:
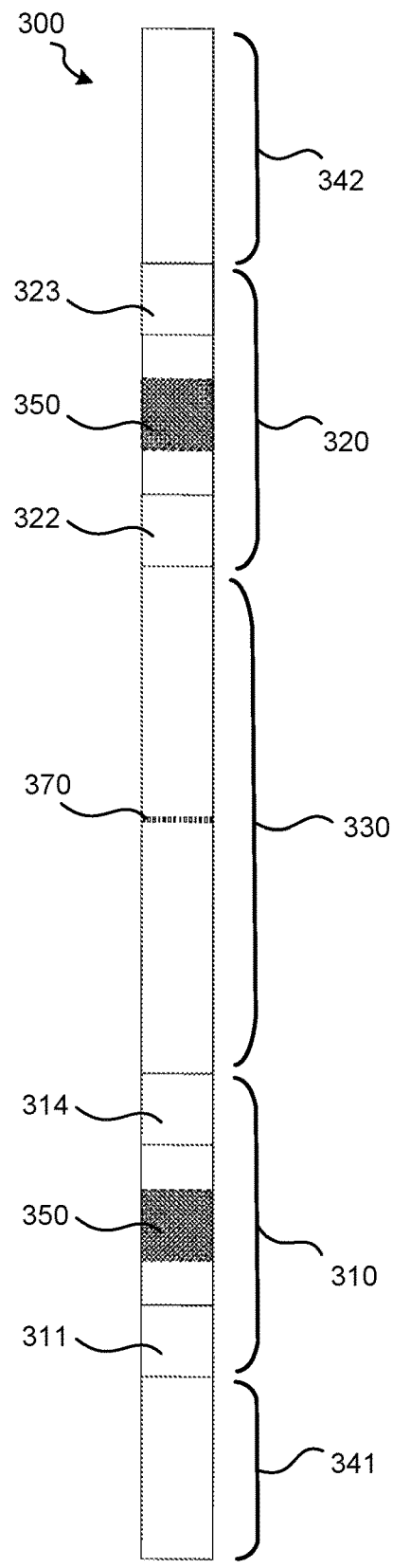
FIG. 3A is a front view of a multi-fluid test strip, according to another embodiment of the present disclosure.

FIG. 3A shows a front view of a multi-fluid test strip 300, according to another embodiment of the present disclosure. The multi-fluid test strip 300 may include similar features to the multi-fluid test strip 200 of FIGS. 2A-2C, such as: a first zone 310, a first test pad 311, a second zone 320, a second test pad 322, a third test pad 323, a fourth test pad 314, a third zone 330, a first grip zone 341, a second grip zone 342, and one or more barriers 350. However, the multi-fluid test strip 300 may also include additional features, such as a perforation 370 in the third zone 330 of the multi-fluid test strip 300. The perforation 370 may allow the user to separate the first zone 310 from the second zone 320 to further reduce or eliminate the risk of cross-contamination between fluids during testing. It will be understood that any of the test strips disclosed herein may also include a suitable perforation to allow separation of the first zone from the second zone for a given test strip.

The perforation 370 may have any structure suitable for facilitating separation of the two ends of the multi-fluid test strip 300 from each other. The perforation 370 may be configured such that separation can easily be performed by hand. Alternatively, the perforation 370 may facilitate separation through the use of a break feature on a tool or container, such as a pair of scissors, a serrated edge of the container housing multiple multi-fluid test strips 300, and/or the like.

Figure 3B:
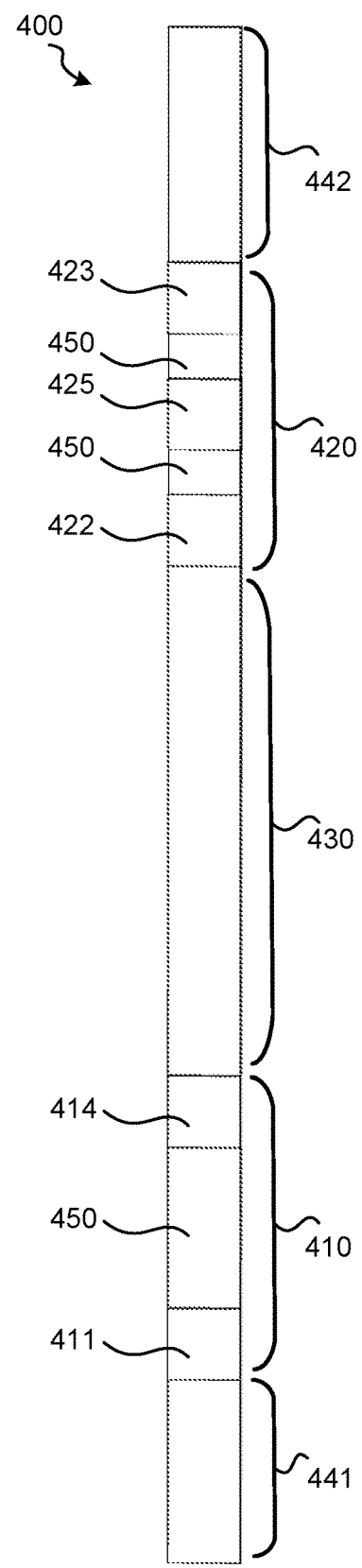
FIG. 3B is a front view of a multi-fluid test strip, according to another embodiment of the present disclosure.

FIG. 3B shows a front view of a multi-fluid test strip 400, according to another embodiment of the present disclosure. The multi-fluid test strip 400 may include similar features to the multi-fluid test strip 200 of FIGS. 2A-2C, such as: a first zone 410, a first test pad 411, a second zone 420, a second test pad 422, a third test pad 423, a fourth test pad 414, a third zone 430, a first grip zone 441, a second grip zone 442, and one or more barriers 450. However, the multi-fluid test strip 400 may also include additional features, such as a fifth test pad 425. Moreover, the one or more barriers 450 may include suitable lengths of test strip between the test pads, as shown in FIGS. 2A-2C. It will be understood that any of the test strips disclosed herein may also include any number or style of barriers between test pads to help reduce or prevent cross-contamination between test pads.

FIG. 4A shows a front view of a multi-fluid test strip 500, according to another embodiment of the present disclosure. The multi-fluid test strip 500 may include similar features to the multi-fluid test strip 200 of FIGS. 2A-2C, such as: a first zone 510, a first test pad 511, a second zone 520, a second test pad 522, a third test pad 523, a fourth test pad 514, a third zone 530, a first grip zone 541, a second grip zone 542, and one or more barriers 550. However, the multi-fluid test strip 500 may also include additional features, such as a fifth test pad 525, a sixth test pad 526, a seventh test pad 517, and an eighth test pad 518.

As shown in FIG. 4A, the test pads 511, 514, 517, 518, 522, 523, 525, 526 may be spaced apart from each other perpendicular to a length of the multi-fluid test strip 500. Likewise, the one or more barriers 550 may also be spaced apart from each other perpendicular to a length of the multi-fluid test strip 500. It will be understood that any of the test strips disclosed herein may include any number of test pads arranged along a length of the test strip, spaced apart from each other perpendicular to a length of the test strip, spaced apart from each other at any angle relative to a length of the test strip, placed in a non-uniform pattern, and/or staggered in any manner to help prevent cross-contamination. Moreover, it will be understood that the length and/or width of any test strip disclosed herein may be varied to accommodate any number of test pads arranged, and/or spaced apart from each other, in any fashion.

It will also be understood that any of the test strips disclosed herein may be placed onto a suitable color readout chart (not shown), such as a card with a boundary in the center where a test strip may be placed. The test strip may further be secured to the color readout chart by any suitable means including, but not limited to: cuts formed in the color readout chart, adhesive, holders, etc. The test pads may be positioned near appropriate color charts corresponding to fluid metrics of interest. In at least one embodiment, a single color chart may be used for multiple fluids. In other embodiments, a series of color charts may be used for one or more fluids.

Figure 5A:
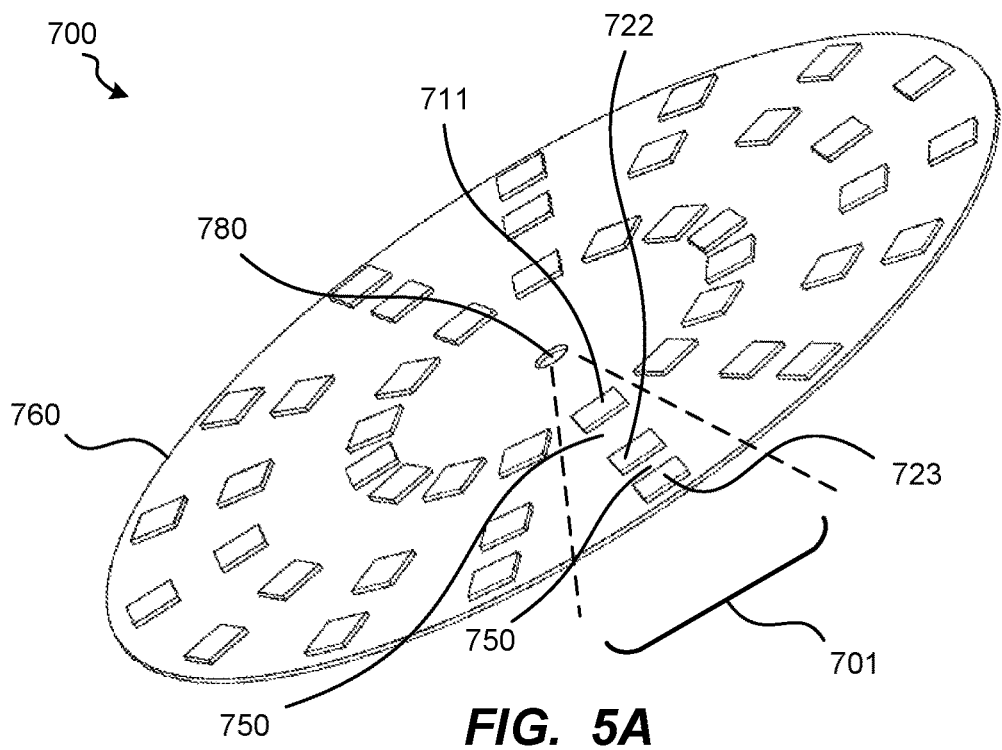
FIG. 5A is an isometric view of a multi-fluid test disk, according to another embodiment of the present disclosure.
Figure 5B:
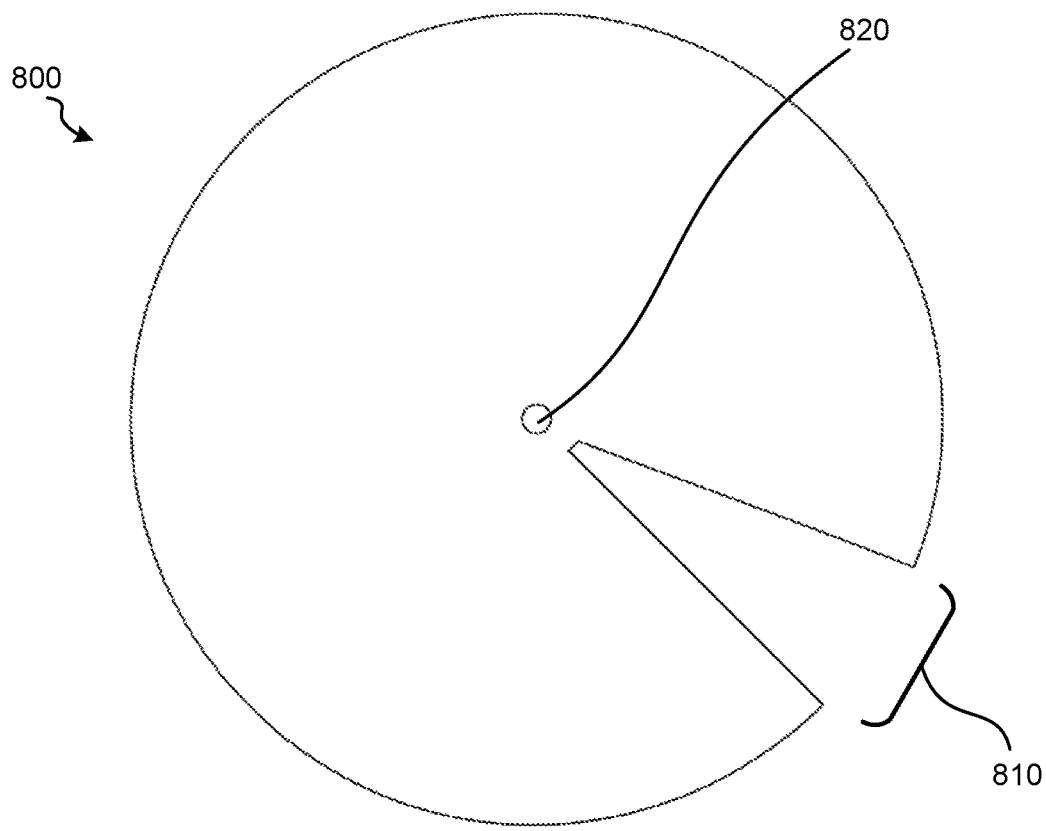
FIG. 5B is a top view of a holder that may be used with the multi-fluid test disk of FIG. 5A.

FIGS. 5A and 5B illustrate a multi-fluid test disk 700 and a holder 800, according to another embodiment of the present disclosure. The multi-fluid test disk 700 may include a substrate 760, one or more test zones 701, a first test pad 711, a second test pad 722, a third test pad 723, and one or more barriers 750.

The substrate 760 may have a generally circular shape and the one or more test zones 701 may be arranged around the substrate 760 in a circular fashion, having pie or wedge shapes. The substrate 760 may also have an aperture 780 formed in the center of the substrate 760 that is configured to receive a connector (not shown) that may couple the substrate 760 to the holder 800 which may have a corresponding holder aperture 810. The holder 800 may also have a window 810 formed therein. The holder 800 may be rotatably coupled to the substrate 760. The user may rotate the holder 800 relative to the substrate 760 such that the window 810 of the holder 800 may be placed over a selected test zone 701. Once the user has selected a test zone 701, the user may apply one or more fluids to the test pads 711, 722, 723 of the selected test zone 701 to test various aspects or metrics of the one or more fluids, as previously discussed.

In at least one embodiment, the user may remove at least a portion of a brake fluid from a container (not shown), such as a brake fluid reservoir on a vehicle, and place the at least a portion of a brake fluid on the first test pad 711. The user may also remove at least a portion of a coolant fluid from a container (not shown), such as a coolant reservoir on a vehicle, and place the at least a portion of the coolant fluid on the second test pad 722 and the third test pad 723. The user may also rotate the holder 800 such that the window 810 formed in the holder 800 reveals another test zone 701 that has not been used, and repeat this process. In this manner, the user may utilize the multi-fluid test disk 700 to perform multiple multi-fluid tests. It will be understood that in other embodiments, the number of test zones 701 may vary by any number, and the number and arrangement of test pads for each test zone may also vary by any number. In some embodiments, the holder 800 may have a color chart or other indicator (not shown) placed on the holder 800. The color chart or other indicator may help the user evaluate the appearance of one or more test pads that are visible through the window 810 of the holder 800 via comparison of the appearance of the pad with the color chart or other indicator.

The test pads 711, 722, 723 of each test zone 701 may be separated from each other by barriers 750, which may include cross-hatching, mechanical barriers, and/or suitable lengths of test strip material, similar to other embodiments previously discussed. Moreover, individual test zones 701 may also be separated from each other by barriers, which may also include cross-hatching, mechanical barriers, and/or suitable lengths of test strip material.

Similar to the multi-fluid test disk 700 and holder 800 of FIGS. 5A and 5B, a multi-fluid test slider (not shown) is also envisioned, according to another embodiment of the present disclosure. The multi-fluid test slider may include similar features to the multi-fluid test disk 700, such as a substrate. However, the substrate may have any shape (e.g., rectangular, square, circular, triangular, etc.). The substrate may also include multiple test pads that may be arranged into discrete test zones and the discrete test zones may be arranged on the substrate in any manner. The substrate may be housed in a slidable holder (not shown) with or without a window formed therein. The user may select a test zone by sliding the slidable holder relative to the substrate to reveal different discrete test zones arranged on the substrate. The user may perform fluid testing by placing fluids on the different test pads of a given test zone, similar to that discussed above. The user may slide the holder such that another test zone is revealed and repeat this process. In this manner, the user may utilize the multi-fluid test slider to perform multiple multi-fluid tests. It will be understood that at least the following characteristics of the multi-fluid test slider may vary in any manner: (1) the size and shape of the substrate; (2) the number of test zones on the substrate, and their arrangement; (3) the number, type, and arrangement of test pads in each test zone; and (4) the number, type, and arrangement of barriers between individual test pads and between individual test zones.

Figure 6A:
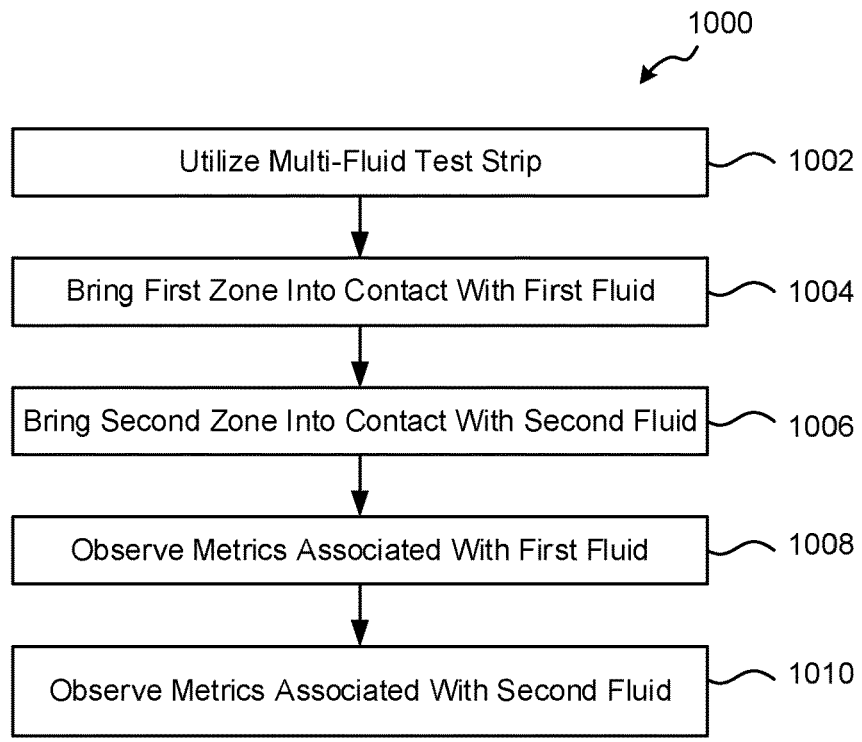
FIG. 6A is a flowchart illustrating a method of utilizing a multi-fluid test strip to test multiple fluids.

FIG. 6A illustrates a flowchart of a method 1000 by which a multi-fluid test strip 100 may be utilized to test multiple fluids. The method 1000 may begin with a step 1002 in which a multi-fluid test strip 100 may be obtained for utilization. The multi-fluid test strip 100 may include a first zone 110, a second zone 120, a third zone 130, and a substrate 160. The first zone 110 may be configured to test a first fluid and the second zone 120 may be configured to test a second fluid. The third zone 130 may be intermediate the first zone 110 and the second zone 120 and configured to prevent cross-contamination of the first fluid with the second zone 120 and prevent cross-contamination of the second fluid with the first zone 110. Once the multi-fluid test strip 100 has been obtained for utilization, the method 1000 may proceed to a step 1004 in which the first zone 110 of the multi-fluid test strip 100 may be brought into contact with the first fluid, such that the third zone 130 avoids contamination of the second zone 120 with the first fluid. In at least one embodiment, bringing the first zone 110 into contact with the first fluid may include removing at least a portion of the first fluid and placing the at least a portion of the first fluid on the first zone 110. In this manner, the user may reduce the likelihood of cross-contamination by controlling the amount/placement of the first fluid.

Once the first zone 110 of the multi-fluid test strip 100 has been brought into contact with the first fluid, the method 1000 may proceed to a step 1006 in which the second zone 120 of the multi-fluid test strip 100 may be brought into contact with the second fluid, such that the third zone 130 avoids contamination of the first zone 110 with the second fluid. In at least one embodiment, bringing the second zone 120 into contact with the second fluid may include removing at least a portion of the second fluid and placing the at least a portion of the second fluid on the second zone 120. The user may reduce the likelihood of cross-contamination by controlling the amount/placement of the second fluid.

Once the second zone 120 of the multi-fluid test strip 100 has been brought into contact with the second fluid, the method 1000 may proceed to a step 1008 in which one or more metrics associated with the first fluid may be observed by the user. The one or more metrics associated with the first fluid may be created by the first zone 110 reacting with the first fluid to produce one or more color changes or other changes in appearance, depending on the type of testing associate with the first zone 110.

Once the one or more metrics associated with the first fluid have been observed, the method 1000 may proceed to a step 1010 in which one or more metrics associated with the second fluid may be observed by the user. The one or more metrics associated with the second fluid may be created by the second zone 120 reacting with the second fluid to produce one or more color changes or other changes in appearance, depending on the type of testing associate with the second zone 120.

Figure 6B:
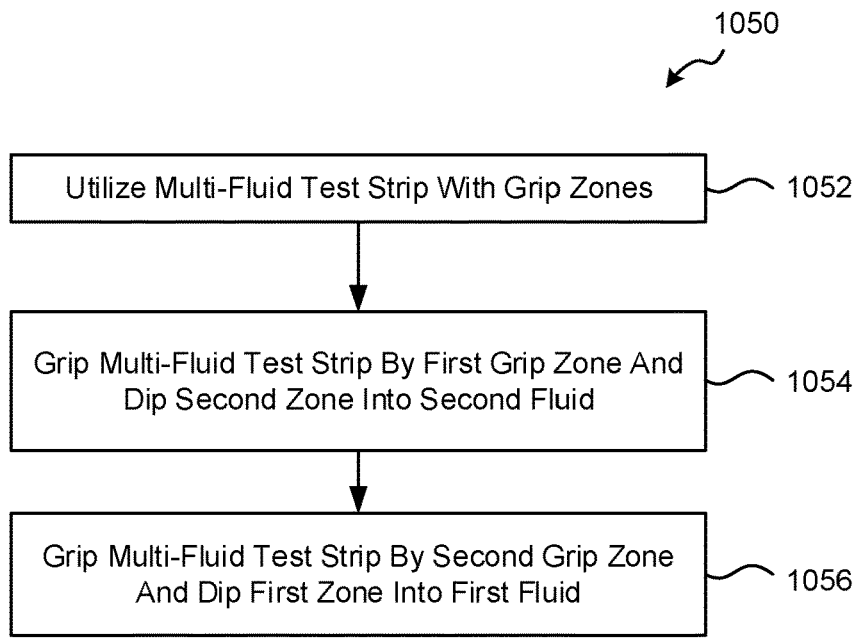
FIG. 6B is a flowchart illustrating a method of bringing multiple fluids into contact with a multi-fluid test strip.

FIG. 6B illustrates a flowchart of a method 1050 by which multiple fluids may be brought into contact with a multi-fluid test strip 100. The method 1050 may begin with a step 1052 in which a multi-fluid test strip 100 may be obtained for utilization. The multi-fluid test strip 100 may be similar to that discussed above with reference to method 1000 and may further include a first grip zone 141 and a second grip zone 142. The first zone 110 may be intermediate the first grip zone 141 and the third zone 130. Likewise, the second zone 120 may be intermediate the second grip zone 142 and the third zone 130. The first grip zone 141 may be dimensioned to permit gripping of the first grip zone 141 without touching the first zone 110 and, similarly, the second grip zone 142 may be dimensioned to permit gripping of the second grip zone 142 without touching the second zone 120.

Once the multi-fluid test strip 100 has been obtained for utilization, the method 1050 may proceed to a step 1052 in which the multi-fluid test strip 100 may be gripped by the first grip zone 141 and the second zone 120 of the multi-fluid test strip 100 may be dipped into the second fluid. In one embodiment, the user may use his/her fingers to grip the first grip zone 141. In another embodiment, the user may use a gripping tool, such as an alligator clip, to grip the first grip zone 141 by coupling the multi-fluid test strip 100 to the gripping tool.

Once the second zone 120 of the multi-fluid test strip 100 has been dipped into the second fluid, the method 1050 may proceed to a step 1056 in which the multi-fluid test strip 100 may be gripped by the second grip zone 142 and the first zone 110 of the multi-fluid test strip 100 may be dipped into the first fluid. In one embodiment, the user may use his/her fingers to grip the second grip zone 142. In another embodiment, the user may use a gripping tool, such as an alligator clip, to grip the second grip zone 142 by coupling the multi-fluid test strip 100 to the gripping tool.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it will be appreciated that in the above description of embodiments, various features are sometimes grouped together in a single embodiment, figure, or description for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Only elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure herein without departing from the spirit and scope of the disclosure.

What is claimed is:

1. A multi-fluid test strip comprising:
   a first zone configured to test a first fluid;
   a second zone configured to test a second fluid; and
   a third zone configured to prevent cross-contamination of the first fluid with the second zone and the second fluid with the first zone, the third zone intermediate the first zone and the second zone.

2. The multi-fluid test strip of claim 1, further comprising a first grip zone and a second grip zone, the first zone intermediate the first grip zone and the third zone and the second zone intermediate the second grip zone and the third zone, wherein the first grip zone is dimensioned to permit gripping of the first grip zone without touching the first zone and the second grip zone is dimensioned to permit gripping of the second grip zone without touching the second zone.

3. The multi-fluid test strip of claim 2, wherein the first zone comprises a first test pad configured to test a first aspect of the first fluid and the second zone comprises a second test pad configured to test a second aspect of the second fluid.

4. The multi-fluid test strip of claim 3, wherein the second zone further comprises a third test pad configured to test a third aspect of the second fluid, wherein the second test pad and the third test pad are separated from each other by a barrier.

5. The multi-fluid test strip of claim 4, wherein the barrier comprises a cross-hatch zone formed in the multi-fluid test strip and configured to reduce or prevent flow between the second test pad and the third test pad.

6. The multi-fluid test strip of claim 4, wherein the barrier comprises a mechanical barrier configured to reduce or prevent flow between the second test pad and the third test pad.

7. The multi-fluid test strip of claim 4, wherein the second test pad and the third test pad are spaced apart from each other along a length of the multi-fluid test strip.

8. The multi-fluid test strip of claim 4, wherein the second test pad and the third test pad are spaced apart from each other perpendicular to a length of the multi-fluid test strip.

9. The multi-fluid test strip of claim 4, wherein:
   the third zone comprises a length greater than about 2.5 inches;
   the first fluid comprises a brake fluid;
   the second fluid comprises a coolant fluid;
   the first test pad is configured to test a first metric associated with the brake fluid by reacting with the brake fluid to produce a first color change representative of the first metric associated with the brake fluid, wherein the first metric includes at least one of a copper level, an iron level, a DOT fluid type, and a first pH level of the brake fluid; and
   the second test pad and the third test pad are configured to test a second metric and a third metric associated with the coolant fluid by reacting with the coolant fluid to produce a second color change and a third color change representative of the second metric and the third metric associated with the coolant fluid, wherein the second metric and the third metric includes at least one of a glycol level, a reserve alkalinity, and a second pH level of the coolant fluid, and wherein the second test pad and the third test pad are configured to produce a substantially similar second color change and a substantially similar third color change for more than one type of coolant fluid.

10. The multi-fluid test strip of claim 1, wherein the third zone comprises a length ranging from about 0.6 inches to about 0.8 inches.

11. A method of testing multiple fluids, the method comprising:
    utilizing a multi-fluid test strip comprising:
       a first zone configured to test a first fluid;
       a second zone configured to test a second fluid; and
       a third zone configured to prevent cross-contamination of the first fluid with the second zone and the second fluid with the first zone, the third zone intermediate the first zone and the second zone;
    bringing the first zone into contact with the first fluid such that the third zone avoids contamination of the second zone with the first fluid;
    bringing the second zone into contact with the second fluid such that the third zone avoids contamination of the first zone with the second fluid;
    observing one or more metrics associated with the first fluid created by the first zone reacting with the first fluid; and
    observing one or more metrics associated with the second fluid created by the second zone reacting with the second fluid.

12. The method of claim 11, further comprising:
    utilizing a multi-fluid test strip that further includes a first grip zone and a second grip zone, the first zone intermediate the first grip zone and the third zone and the second zone intermediate the second grip zone and the third zone, wherein bringing the first zone into contact with the first fluid and bringing the second zone into contact with the second fluid further comprises:

gripping the multi-fluid test strip by the first grip zone and dipping the second zone of the multi-fluid test strip into the second fluid such that the third zone avoids contamination of the first zone with the second fluid; and gripping the multi-fluid test strip by the second grip zone and dipping the first zone of the multi-fluid test strip into the first fluid such that the third zone avoids contamination of the second zone with the first fluid.

13. The method of claim 12, wherein gripping the multi-fluid test strip comprises coupling the multi-fluid test strip to a gripping tool.

14. The method of claim 11, wherein bringing the first zone into contact with the first fluid and bringing the second zone into contact with the second fluid comprises:

removing at least a portion of the first fluid and placing the at least a portion of the first fluid on the first zone; and
removing at least a portion of the second fluid placing the at least a portion of the second fluid on the second zone.

15. The method of claim 11, further comprising:

utilizing a multi-fluid test strip wherein the first zone and the second zone of the multi-fluid test strip further includes one or more test pads configured to test the one or more metrics associated with the first fluid and the second fluid, the first fluid comprising a brake fluid, the second fluid comprising a coolant fluid, and the one or more test pads configured to test the one or more metrics associated with the brake fluid and the coolant fluid by reacting with one of the brake fluid and the coolant fluid to produce one or more color changes representative of the one or more metrics associated with the brake fluid and the coolant fluid, and wherein the third zone comprises a length greater than about 2.5 inches.

16. The method of claim 15, wherein the one or more metrics include at least one of a copper level, an iron level, a DOT fluid type, and a first pH level of the brake fluid, and at least one of a glycol level, a reserve alkalinity, and a second pH level of the coolant fluid.

17. The method of claim 11, further comprising:

utilizing a multi-fluid test strip wherein the third zone comprises a length ranging from about 0.6 inches to about 0.8 inches.

18. A multi-fluid test strip comprising:

a first zone configured to test a first fluid, the first zone comprising a first test pad configured to test a first aspect of the first fluid;

a second zone configured to test a second fluid, the second zone comprising a second test pad and a third test pad configured to test a second aspect and a third aspect of the second fluid;

a third zone intermediate the first zone and the second zone, the third zone configured to prevent cross-contamination of the first fluid with the second zone and prevent cross-contamination of the second fluid with the first zone;

a first grip zone, the first zone intermediate the first grip zone and the third zone, wherein the first grip zone is dimensioned to permit gripping of the first grip zone without touching the first zone; and a second grip zone, the second zone intermediate the second grip zone and the third zone, wherein the second grip zone is dimensioned to permit gripping of the second grip zone without touching the second zone.

19. The multi-fluid test strip of claim 18, wherein:

the third zone comprises a length greater than about 2.5 inches;
the first fluid comprises a brake fluid;
the second fluid comprises a coolant fluid;
the first test pad is configured to test a first metric associated with the brake fluid by reacting with the brake fluid to produce a first color change representative of the first metric associated with the brake fluid, wherein the first metric includes at least one of a copper level, an iron level, a DOT fluid type, and a first pH level of the brake fluid; and
the second test pad and the third test pad are configured to test a second metric and a third metric associated with the coolant fluid by reacting with the coolant fluid to produce a second color change and a third color change representative of the second metric and the third metric associated with the coolant fluid, wherein the second metric and the third metric includes at least one of a glycol level, a reserve alkalinity, and a second pH level of the coolant fluid, and wherein the second test pad and the third test pad are configured to produce a substantially similar second color change and a substantially similar third color change for more than one type of coolant fluid.

20. The multi-fluid test strip of claim 18, wherein the third zone comprises a length ranging from about 0.6 inches to about 0.8 inches.

* * * * *